US011268060B2

(12) United States Patent
Pawell

(10) Patent No.: US 11,268,060 B2
(45) Date of Patent: Mar. 8, 2022

(54) METHOD FOR MECHANICAL AND HYDRODYNAMIC MICROFLUIDIC TRANSFECTION AND APPARATUS THEREFOR

(71) Applicant: Indee. Inc., Wilmington, DE (US)

(72) Inventor: Ryan Pawell, Maroubra (AU)

(73) Assignee: Indee. Inc.

(*) Notice: Subject to any disclaimer, the term of this patent is extended or adjusted under 35 U.S.C. 154(b) by 0 days.

(21) Appl. No.: 15/497,122

(22) Filed: Apr. 25, 2017

(65) Prior Publication Data
US 2017/0233692 A1 Aug. 17, 2017

Related U.S. Application Data

(63) Continuation of application No. PCT/AU2015/050748, filed on Nov. 26, 2015.

(30) Foreign Application Priority Data

Jan. 7, 2015 (AU) .............................. 2015900021

(51) Int. Cl.
| C12N 15/87 | (2006.01) |
| B81B 1/00 | (2006.01) |
| C12M 1/42 | (2006.01) |
| C12M 1/00 | (2006.01) |
| C12M 3/06 | (2006.01) |

(52) U.S. Cl.
CPC .............. C12M 35/04 (2013.01); B81B 1/00 (2013.01); C12M 23/16 (2013.01); C12M 27/18 (2013.01); C12M 35/00 (2013.01); C12N 15/87 (2013.01); *B81B 2201/058* (2013.01); *B81B 2203/0338* (2013.01); *C12N 2510/00* (2013.01); *C12N 2521/00* (2013.01); *C12N 2740/15043* (2013.01)

(58) Field of Classification Search
None
See application file for complete search history.

(56) References Cited

U.S. PATENT DOCUMENTS

| 5,658,892 A | 8/1997 | Flottee et al. |
| 5,720,921 A | 2/1998 | Meserol |
| 6,563,623 B1 | 5/2003 | Rickwood |
| 8,304,230 B2 | 11/2012 | Toner et al. |
| 8,372,579 B2 | 2/2013 | Toner et al. |
| 8,529,026 B2* | 9/2013 | Clarke ................ B01F 13/0062 347/73 |
| 8,895,298 B2 | 11/2014 | Toner et al. |
| 8,986,966 B2 | 3/2015 | Toner et al. |
| 9,017,991 B2 | 4/2015 | Diefenbach |
| 2003/0017578 A1 | 1/2003 | Ueberle et al. |
| 2005/0032212 A1 | 2/2005 | Rickwood |
| 2005/0123563 A1* | 6/2005 | Doranz ................. A61K 39/12 424/204.1 |
| 2007/0231851 A1 | 10/2007 | Toner et al. |
| 2012/0006760 A1 | 1/2012 | Toner et al. |
| 2012/0064518 A1* | 3/2012 | Diefenbach ............ C12N 15/89 435/6.1 |
| 2014/0287509 A1 | 9/2014 | Sharei et al. |
| 2015/0260711 A1 | 9/2015 | Toner et al. |
| 2015/0284741 A1 | 10/2015 | Diefenbach |

FOREIGN PATENT DOCUMENTS

| JP | 2005287419 A | 10/2005 |
| WO | 1996/024360 A1 | 8/1996 |
| WO | 1998/13470 A1 | 4/1998 |
| WO | 2001/005994 A2 | 1/2001 |
| WO | 2003/016541 A1 | 2/2003 |
| WO | 2004/029221 A2 | 4/2004 |
| WO | 2008/021465 A2 | 2/2008 |
| WO | 2012/106536 A2 | 8/2012 |

OTHER PUBLICATIONS

Wang et al, (Lab Chip, 2010, 10: 2057-2061.*
Ghanem et al., Renewable Energy, 2013, 56: 96-104.*
Hans et al., Measurement, 2003, 33: 121-133.*
Lee et al., J. Micromechanical Systems, 2002, 11: 236-244.*
Che et al., PLOS One, 2013, 8: 1-9.*
Chung et al., Lab Chip, 2013, 13: 2942-2949.*
Caplan et al., J. Embryol. Exp. Med., 1976, 36: 175-181.*
Liu, Biomicrofluidics, 2013, 7: 1-10.*
Sollier, Lab Chip 2014, 14: 63-77.*
Kim, Lab Chip, 2011, 11: 3941-3948.*
Hejna et al., Nucleic Acids Research, 1998, 26: 1124-1125.*
Proc. Symp. Ultrason. Electron., 2006, vol. 27, pp. 371-374.
Sharei et al., A vector-free microfluidic platform for intracellular delivery, Proc Natl Acad Sci USA. Feb. 5, 2013;110(6):2082-7. doi: 10.1073/pnas.1218705110. Epub Jan. 22, 2013.
Database WPI, Week 200575, Thomson Scientific, London, GB, AN 2005-729019, XP002783751.
Unal, M.F. et al., On Vortex Formation From a Cyclinder, part 2. Control by splitter-plate interference, J. Fluid Mech., vol. 190, pp. 513-529 (1987).
Jarrell, Justin et al., Intracellular delivery of mRNA to human primary T cells with microfluidic vortex shedding, Scientific Reports, https://doi.org/10.1038/s41598-019-40147-y, (2019) 9:3214.
Stadtmauer, Edward et al., CRISPER-engineered T cells in patients with refractory cancer, Science, 10.1126/science.aba7365 (2020).

(Continued)

*Primary Examiner* — Ileana Popa

(74) *Attorney, Agent, or Firm* — Southern Cross Intellectual Property

(57) ABSTRACT

Methods for introducing exogenous material into a cell are provided, which include exposing the cell to a transient decrease in pressure in the presence of the exogenous material. Also provided are devices for performing the method of the invention.

30 Claims, 7 Drawing Sheets

(56) References Cited

OTHER PUBLICATIONS

Stewart, Martin P. et al., Invitro and ex vivo strategies for intracellular delivery, doi:10.1038/nature19764, vol. 538, pp. 183-192 (Oct. 13, 2016).

Ghassemi, Saba et al., Reducing Ex Vivo Culture Improves teh Anti-leukemic Activity of Chimeric Antigen Receptor (CAR) T Cells, DOI 10.1158/2326-6066 (Jul. 20, 2018)(27 pages).

\* cited by examiner

METHOD FOR MECHANICAL AND HYDRODYNAMIC MICROFLUIDIC TRANSFECTION AND APPARATUS THEREFOR

CROSS REFERENCE TO RELATED APPLICATIONS

This application is a continuation of International Application No. PCT/AU2015/050748, filed 26 Nov. 2015, which claims the benefit of Australian Provisional Application No. 2015900021, filed 7 Jan. 2015. The entire contents of each of the above-identified applications is hereby incorporated by reference herein.

FIELD OF THE INVENTION

The invention relates to a method for introducing exogenous material into a cell, comprising exposing the cell to a transient decrease in pressure in the presence of the exogenous material. The transient decrease in pressure is preferably coupled with an unsteady flow of liquid in which the cell and exogenous material are present. In particular, the invention relates to transfection of mammalian cells.

BACKGROUND OF THE INVENTION

Any discussion of the prior art throughout the specification should in no way be considered an admission that such prior art is widely known or forms part of common general knowledge in the field.

The introduction of exogenous material such as small organic molecules, proteins and nucleic acids into cells in vitro and in vivo is crucial for the progression of research and development of therapies, as well as therapeutic delivery strategies.

For example, the introduction of fluorescently tagged proteins into cells allows real time analysis of the trafficking of the proteins throughout the cells, which may also assist in the identification of protein interactions during clinically important stages of a disease, or in response to specific triggers. Introducing putative small organic molecule drugs, which do not naturally cross cell membranes effectively, into cells during drug development can be informative on the activity of said drugs prior to diverting valuable time and effort towards developing delivery vehicles for these drugs.

The introduction of nucleic acids into cells is a critical step in cell therapy manufacturing, where expression vectors encoding genes are delivered across the cell membrane into the cytoplasm to effectively engineer live cells that can be used as therapeutic agents. By way of example, cell therapy may be used to induce an individual's own immune system to attack cancer cells or evade a virus, such as HIV. Cancer and HIV are of particular relevance from a global health perspective given their prevalence in the population with an estimated 35 million HIV patients in 2013 and 14 million new cancer cases in 2012. Utilising cell-derived gene therapy as part of a global health strategy requires a cell therapy manufacturing method capable of reproducibly producing sufficient quantities of product to potentially treat tens of millions of patients per annum at the appropriate price point and under current Good Manufacturing Practice in accordance with regulatory standards.

Accordingly, the ability to introduce exogenous material and in particular nucleic acids into cells in a quick and efficient manner is both a valuable research tool and a useful component of a therapeutic strategy.

There are several known methods for introducing agents into cells, with the choice of method generally being determined by the type of cell, the level of efficiency required, the size of the molecule being introduced and the number of cells available.

Although the terms may be used interchangeably, the introduction of agents such as nucleic acids into eukaryotic cells is generally referred to as "transfection", whereas the introduction of nucleic acid into prokaryotic cells is generally referred to as "transformation". Transfection and transformation methods may be conveniently separated into three categories, namely, chemical, physical and viral-based methods.

Chemical methods of transfection employ reagents such as cationic lipids, calcium phosphate, cationic polymers and dendrimer molecules to essentially package the nucleic acids for delivery into the cell. However, many of these methods are not applicable to all cell types. Moreover, they can be compromised by pH fluctuations or salts/phosphates in the cell media. Due to the requirement for packaging of nucleic acids in some of these methods, the size of the nucleic acid molecules that can be accommodated may be limited. Further, chemical transfection methods can require use of reagents that are expensive and/or toxic to cells in high concentrations and/or the method may only achieve low/inconsistent transfection efficiencies.

Conventional physical methods used to transfect eukaryotic cells include the use of magnetic nanoparticles, electroporation, bolistic particle delivery and microinjection. However, these methods tend to be quite harsh on the cells, often resulting in high mortality rates. These methods may also require immobilised cells, expensive equipment and/or a greater degree of technical skill on the part of the person performing the method. For example, in some electroporation methods, suspended cells are first permeabilised, followed by the application of an electric field to facilitate active delivery of charged exogenous material. Hence these techniques require specialised equipment and consumables for permeabilising the membranes of the cells and applying the electrical field.

Viral-based transfection methods rely on viral vectors including lentiviral, adenoviral and retroviral vectors for the delivery of nucleic acids into a cell, where the nucleic acids may be expressed at high levels by virtue of a viral promoter. These viral-based methods are expected to prove useful for the effective treatment of cancers of the lymphatic and haematopoietic systems, and for HIV therapeutics. However, due to variable transfection efficiencies, the cost of manufacturing viral vectors for these types of therapeutics is in the order of thousands of dollars per patient. Further, this method can be both labour intensive and prone to manufacturing issues if the process is not automated.

The introduction of exogenous material, and in particular, nucleic acids, into prokaryotic cells is also an important aspect for the manufacture of biologics during therapeutic drug development and indeed, research in general. Transformation of bacterial cell lines with exogenous nucleic acids for the recombinant production of valuable molecules such as biologic-based pharmaceuticals (so called biopharmaceuticals) can be achieved by various methods including chemical transformation and electroporation. However, these methods may require that the cells be made "competent" prior to transformation (e.g., by inducing high cell density and/or nutritional limitation which switches on a set of genes), they may not be applicable to all cell types and/or they may result in high levels of cell mortality.

Consequently, there is a need for a fast and efficient method of introducing exogenous material into a range of cell types that overcomes one or more of the difficulties of the known methods. Preferably, the method would deliver an acceptable level of cell viability and it would be cost-effective.

It is an object of the invention to overcome or ameliorate at least one of the disadvantages of the prior art, or to provide a useful alternative.

It will be appreciated that reference herein to "preferred" or "preferably" is intended as exemplary only.

SUMMARY OF THE INVENTION

The limitations associated with the introduction of exogenous material into cells are often related to the toxicity and/or expense associated with the reagents and devices used for physical, viral and chemical transfection and transformation methods. Further, many transfection methods are not adaptable to high-throughput applications partly because they require significant human intervention throughout the process and large volumes of cells to compensate for the low transfection efficiencies and/or cell viabilities. Indeed, human intervention is often the source of the inconsistencies associated with the transfection efficiencies of methods that are heavily reliant on technicians. The introduction of even low levels of imprecision by humans can have significant adverse effects on delivery efficiency, cell viability and/or repeatability. See, for example Mitsuyasu et al. (Mitsuyasu R. T., et al. (2009). Phase 2 gene therapy trial of an anti-HIV ribozyme in autologous CD34+ cells. Nature Medicine, 15(3):285-292) wherein viral vectors were used to transfect CD34+ hematopoietic progenitor cells resulting in 54±17% (mean±standard deviation) delivery efficiencies across 38 patients (n=38).

It has been surprisingly found by the inventor that, when exposed to a transient decrease in pressure, cells are susceptible to the uptake of exogenous material.

Without wishing to be bound by theory, the transient decrease in pressure most likely permeabilises the cell membrane without lysing the cell. A relatively sudden and temporary pressure drop across the cell membrane, whereby the intracellular pressure is greater than the extracellular pressure, may result in the temporary formation of pores in the membrane allowing for the introduction of the exogenous material.

Accordingly in a first aspect of the invention, there is provided a method for introducing an exogenous material into a cell, comprising exposing the cell to a transient decrease in pressure in the presence of said exogenous material to thereby introduce said exogenous material into said cell. The transient decrease in pressure does not result in the cell being lysed although in certain embodiments it may be rendered non-viable. The skilled addressee will understand that when the invention is applied to a population of cells, some of the cells in the population may be lysed.

Preferably the cell is viable after being exposed to the transient decrease in pressure.

Preferably, the cell is selected from the group consisting of a bacterial cell, a mammalian cell, a yeast cell, a plant cell and an insect cell.

In certain preferred embodiments, the cell is a mammalian cell. In other preferred embodiments, the cell is a bacterial cell. In yet other preferred embodiments, the cell is a yeast cell. In further preferred embodiments, the cell is an insect cell. In yet further embodiments, the cell is a plant cell.

Preferably the exogenous material is selected from the group consisting of small organic molecule, nucleic acid, nucleotides, proteins, peptides, amino acids, lipids, polysaccharides, viruses, quantum dots, carbon nanotubes, radionuclide, magnetic bead, nanoparticles, gold particles, monosaccharides, vitamins and steroids.

Preferably the nucleic acids are selected from the group consisting of PNA, DNA, RNA, mRNA, miRNA and siRNA.

Preferably the DNA is a plasmid.

Preferably the plasmid is an expression vector.

Preferably the expression vector expresses PNA, DNA, RNA, miRNA, siRNA or protein.

Preferably the expression vector is a viral vector.

Preferably the viral vector is a lentiviral vector or retroviral vector.

Preferably the expression vector is a bacterial artificial chromosome (BAC) or a yeast artificial chromosome (YAC).

Preferably the exogenous material is introduced into the cytoplasm of the cell.

Preferably the exogenous material is introduced into the nucleus of the cell. In these preferred embodiments, the cell is a mammalian cell, a yeast cell, a gamete (e.g., a sperm cell or an ovum cell) or an insect cell. More preferably, the cell is a mammalian cell.

Preferably the transient decrease in pressure is a decrease of at least 10 kPa.

Preferably the transient decrease in pressure is a decrease of at least 100 kPa.

Preferably the transient decrease in pressure is a decrease of at least 500 kPa.

Preferably the transient decrease in pressure is a decrease of at least 1000 kPa.

Preferably the cell is exposed to said transient decrease in pressure in the presence of said exogenous material for at least 10 nanoseconds.

Preferably the cell is exposed to said transient decrease in pressure in the presence of said exogenous material for at least 100 nanoseconds.

Preferably the cell is exposed to said transient decrease in pressure in the presence of said exogenous material for at least 1 microsecond.

Preferably the cell is exposed to said transient decrease in pressure in the presence of said exogenous material for no more than 1 millisecond.

Preferably the exogenous material and said cell are in a liquid when being exposed to said transient decrease in pressure.

Preferably the cell is exposed to said transient decrease in pressure within an enclosed channel with dimensions configured to allow a flow of said liquid comprising said exogenous material and said cell therethrough.

Preferably the flow of said liquid in said channel has a fluctuating velocity.

Preferably the flow has a minimum peak velocity of at least 1 meter per second.

Preferably the flow has a minimum peak velocity of at least 5 meters per second.

Preferably the flow has a maximum peak velocity of no more than 50 meters per second.

Preferably the flow has a maximum peak velocity of no more than 100 meters per second.

Preferably the channel is configured to influence the flow of said liquid such that there are one or more regions within the channel where the flow of said liquid is laminar, and/or one or more regions within the channel where the flow of said liquid is creeping, and/or one or more regions within the channel where the flow of said liquid is unsteady.

Preferably the object Reynolds number ($Re_o$) of the flow of the liquid around a flow diverter in at least one of said regions within the channel is sufficient to induce unsteady flow.

Preferably the object Reynolds number ($Re_o$) is at least 40.

Preferably the object Reynolds number ($Re_o$) is no more than 2000.

Preferably the flow of liquid is influenced by one or more flow diverters within said channel.

Preferably the one or more regions within the channel where the flow of said liquid is unsteady is downstream of said flow diverter.

Preferably the cell is exposed to said transient decrease in pressure downstream of said flow diverter.

Preferably the flow diverter is an obstacle placed within said enclosed channel.

Preferably the obstacle is a post. More preferably, the post is cylindrical.

Preferably the obstacle is positioned in said channel such that said cell must pass through a gap with a width and height, or diameter, at least 1.01× the minimum diameter of said cell when flowing through said channel.

Preferably the gap has a width and height, or diameter, at least 1.01× the minimum diameter of said cell.

Preferably the gap has a width and height, or diameter, at least 2× the minimum diameter of said cell.

Preferably the gap has a width and height, or diameter, at least 10× the minimum diameter of said cell.

Preferably the gap has a width and height, or diameter, at least 100× the minimum diameter of said cell.

Preferably the obstacle has a maximum width of 10 nanometers.

Preferably the obstacle has a maximum width of 20 micrometers.

Preferably the obstacle has a maximum width of 100 micrometers.

Preferably the obstacle has a maximum width of 1 millimetre.

There are numerous advantages to adapting high-throughput methods for introducing exogenous material into cells to meet the demands of large-scale manufacturing. For example, devices such as microfluidic devices, can be suitably designed and operated to expose cells to one or more transient decreases in pressure in the presence of exogenous material. Advantageously, the devices may be manufactured from simple plastics at very low cost, potentially in the range of only a few dollars per device.

Accordingly, in a second aspect of the invention, there is provided a device for use in a method for introducing an exogenous material into a cell in a liquid, comprising;
- an at least partially enclosed channel with dimensions configured to allow the flow of said cell and an exogenous material suspended in a liquid therethrough; and
- one or more flow diverters within said channel;
- wherein the flow diverter results in at least one region of decreased pressure immediately downstream of said flow diverter.

Preferably the region of decreased pressure occurs in at least one region of unsteady flow immediately downstream of said flow diverter.

Preferably the device is a microfluidic device.

Preferably the device is configured according to FIG. 4.
Preferably the device is configured according to FIG. 5.
Preferably the device is configured according to FIG. 6.
Preferably the device is configured according to FIG. 7.
Preferably the device is configured according to FIG. 8.
Preferably the device is configured according to FIG. 9.
Preferably, the device is configured according to FIG. 10.

Preferably the device is used in a method for introducing exogenous material into a cell in a liquid according to any one of previous aspects.

Accordingly, in a third aspect of the invention, there is provided a cell comprising an exogenous material produced according to any one of the previous aspects.

Accordingly, in a fourth aspect of the invention, there provided is a cell suspension comprising a cell of the fourth aspect.

Accordingly, in a fifth aspect of the invention, there is provided a pharmaceutical composition comprising a cell of the third aspect or a cell suspension of the fourth aspect, and a pharmaceutically acceptable diluent, cryopreservant, carrier or excipient.

Accordingly, in a sixth aspect of the invention, there is provided a kit comprising a device of the second aspect.

The invention relates to the introduction of exogenous material into a cell. As used herein, the term "exogenous" means any material that exists outside of the cell prior to the cell being exposed to the transient decrease in pressure in the presence of the exogenous material. It will be understood that the term "exogenous" relates to material that has been developed, grown or originated outside the cell. The exogenous material may be naturally occurring or synthetic. In the context of the present application, the term "naturally occurring" insofar as it relates to a material means any material that exists in nature, and may include biologically active substances. The naturally occurring materials may be modified in ways that do not naturally occur in nature and is suitably isolated from nature by techniques as known in the art. In the context of the present application, the term "synthetic" is meant not naturally occurring, but made through human technical intervention. In the context of synthetic proteins and nucleic acids, this encompasses molecules produced by recombinant, chemical synthetic or combinatorial techniques as are well known in the art. The synthetic material may be an imitation of a naturally occurring material, or may not be analogous to a material that exists in nature.

The exogenous material may be biologically active in the cell into which the material is introduced. Alternatively, the exogenous material may have no detectable effect on the cell after it is introduced.

The cell may be any cell with a cell membrane or cell wall that may be temporarily permeabilised when said cell is exposed to a transient decrease in pressure. The cell may or may not be viable before or after being exposed to the transient decrease in pressure in the method of the invention. The cell may or may not be senescent. As the method of the invention may be a passive method of introducing exogenous material into a cell, it would be understood that it is not essential that the method of the invention be performed on cells that are viable and/or actively dividing. For example, in the event the exogenous material was being introduced into the cell to identify a particular organelle in the cytoplasm, the method of the invention could be performed on dead cells (cells that are no longer capable of metabolising). In another example, if the exogenous material being introduced into the cell was a selective marker for cell death, the method of the invention could be performed on a mixture of live and dead cells.

In particular embodiments of the invention, the cell is a bacterial cell, a mammalian cell, a yeast cell, a gamete cell (e.g., a sperm cell or an ovum cell), a plant cell or an insect cell. It will be appreciated that the invention also contemplates a progenitor cell and in particular a stem cell and more preferably, a hematopoetic stem cell or mesenchymal stem cell. The cell may be in culture, extracted from tissue samples and/or immortalised. It will be appreciated that in those embodiments that contemplate a plant cell, the cell wall is completely or partially removed to form a protoplast, prior to treatment according to the methods of the present invention. The cell may be from a primary culture or may from a continuous (secondary) culture. The cell may be derived from any tissue type. The cell may or may not be terminally differentiated. Suitably, the cell is an isolated cell. By "isolated" is meant material that is substantially or essentially free from components that normally accompany it in its native state, or from components present during its production when purified or produced by synthetic means. Thus, the term "isolated" also includes within its scope purified or synthetic material.

As will be appreciated by a person of skill in the art, preferred starting cell densities may be dependent on the cell type and/or exogenous material. In preferred embodiments of the invention and in particular preferred embodiments that relate to mammalian cells, the starting cell density is between about 2 million cells per mL to about 10 million cell per mL, and all integers in between.

In the context of "introducing exogenous material into a cell" as recited herein, the term "introducing" means that the exogenous material is delivered into, travels into or transfers into at least the outer-most barrier of a cell i.e., into the cell wall or cell membrane. The exogenous material may travel beyond the outer-most barrier of a cell, and pass through the cell wall or cell membrane to enter the cytoplasmic region of the cell. The exogenous material may travel into organelles within the cell. Specifically, the exogenous material may travel into the nucleus of the cell.

In embodiments of the invention, the exogenous material being introduced into the cell is selected from the group consisting of a small organic molecules, a nucleic acid, a nucleotide, an oligonucleotide, a protein, a peptide, an amino acid, a lipid, a polysaccharide, a quantum dot, a nanoparticle, a monosaccharide, a gold particle, a vitamin and a steroid, and combinations thereof. The exogenous material need not have a net charge.

Preferably, the nucleic acid is selected from the group consisting of PNA, DNA, RNA, miRNA and siRNA, and combinations thereof. Preferably, the DNA is an oligonucleotide or plasmid.

In particular embodiments of the invention, the plasmid is an expression vector. An expression vector may be either self-replicating extra-chromosomal vector such as a plasmid, or a vector that integrates into a host genome. As used herein, the term "vector" refers to any molecule used as a vehicle to assist in the delivery or expression of a nucleic acid in a cell. Preferably, the vector expresses DNA, RNA, miRNA, siRNA or protein. By "vector" is meant a polynucleotide molecule, suitably a DNA molecule derived, for example, from a plasmid, bacteriophage, virus, yeast or higher order eukaryote including plant, vertebrate or invertebrate animal, into which a polynucleotide can be inserted or cloned. A vector preferably contains one or more unique restriction sites and can be capable of autonomous replication in a defined host cell including a target cell or tissue or a progenitor cell or tissue thereof, or be integratable with the genome of the defined host such that the cloned sequence is reproducible. Accordingly, the vector can be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector can contain any means for assuring self-replication. Alternatively, the vector can be one which, when introduced into the host cell, is integrated into the genome and replicated together with the chromosome(s) into which it has been integrated. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. In some embodiments, the vector is a viral or viral-derived vector, which is operably functional in vertebrate or invertebrate animal and suitably mammalian cells. Such vector may be derived from a poxvirus, a lentivirus, a retrovirus, an adenovirus or yeast. The vector can also include a selection marker such as an antibiotic resistance gene that can be used for selection of suitable transformants. Examples of such resistance genes are known to those of skill in the art and include the nptII gene that confers resistance to the antibiotics kanamycin and G418 (Geneticin®) and the hph gene, which confers resistance to the antibiotic hygromycin B.

In other embodiments of the invention, the vector is a viral vector, preferably a lentiviral vector or a retroviral vector. The vector may also be a bacterial artificial chromosome or a yeast artificial chromosome.

In the context of the invention, the term "lysed" means that the cell wall/cell membrane of said cell is sufficiently compromised such that the bulk of the content of the cell is no longer contained within the cell wall/cell membrane and the cell is thus rendered non-viable. However, even if a cell is not lysed, it need not necessarily be viable to be useful in the invention. The skilled addressee would appreciate that there may be circumstances when it would be desirable to transfect a cell with exogenous material, without the requirement that the resultant transfected cell be viable, provided the cell is not lysed. For example, in the event the exogenous material was a marker or antibody designed to bind and indicate the location or expression profile of a particular protein in a cell, the cell's viability may not be a determining factor of the assay outcome. In a further example, the method of the invention may result in cells that are not lysed, but are necrotic and still of interest.

In particular embodiments of the invention, the cell is viable after being exposed to the transient decrease in pressure in the method of the invention. It would be understood that a "viable" cell is one that is capable of cellular metabolism and/or cell division. A cell that is capable of cellular metabolism is one that is capable of degrading molecules and releasing energy (generally referred to as catabolism), making molecules (such as polysaccharides, lipids, nucleic acids and proteins) and/or using energy (generally referred to anabolism). A viable cell may be one that is capable of cellular metabolism, but is permanently in the $G_0$ phase of the cell cycle and not capable of cell division.

The method of the invention may be used to transfect a population of cells, and within this population of cells, some cells may be lysed (and hence not viable), some cells may not be lysed but may not be viable, while others may be viable.

As used herein, the term "decrease in pressure" insofar as it relates to exposure of a cell to such a decrease means the cell is exposed to a zone of pressure that is relatively lower than the pressure immediately surrounding the zone. The pressure in the zone may be uniform or may have localised regions of varied pressure provided these localised regions still have a pressure that is lower relative to the pressure surrounding the zone. The pressure surrounding the zone may be uniform or may have localised regions of varied pressure provided these localised regions have a pressure that is higher relative to the zone.

By "pressure" is meant the force per unit area exerted by a substance on its surroundings as is known in the art. The SI unit of pressure is the pascal (Pa). Other commonly used units for the measurement of pressure include kilopascals (kPa), pound forces/square inch (PSI), millimetres of mercury (mmHg), millibars (mbar), and atmospheres (atm) air pressure. Pressure specifically relating to a vacuum may be measured in torrs (Torr). In the present application when the term "kPa" is used, it refers to gauge pressure, not absolute pressure where a gauge pressure of 0 kPa refers to an absolute pressure of 101.325 kPa.

The transient decrease in pressure may be defined in the context of the pressure differential between a zone of lower pressure relative to the pressure of a surrounding zone. The transient decrease in pressure may also be defined in the context of the minimum pressure in the zone of lower pressure and the maximum pressure in the surrounding zones. For example, if the minimum pressure in the zone of lower pressure was −10 kPa and the maximum pressure in the surrounding zone was 100 kPa, then the pressure differential would be 110 kPa. In another example, if the minimum pressure in the zone of lower pressure was 20 kPa and the maximum pressure in the surrounding zone was 500 kPa, then the pressure differential would be 480 kPa. In a further example, the pressure differential between the zone of lower pressure and the surrounding zone may be 200 kPa, which could be the result of the minimum pressure in the zone of lower pressure being in the range of −100 kPa to 1000 kPa and the maximum pressure in the surrounding zone being in the range of 100 kPa to 1200 kPa. In yet another example, the pressure differential between the zone of lower pressure and the surrounding zone may be 50 kPa, which could be the result of the minimum pressure in the zone of lower pressure being in the range of 0 kPa to 150 kPa and the maximum pressure in the surrounding zone being in the range of 50 kPa to 200 kPa.

The maximum and minimum pressure that can be applied to any one cell type will be apparent to the competent skilled addressee. At pressures that are too low, the efficiency of the method may be compromised and at pressures that are too high, the cells may rupture. The optimum pressure differential may be identified for a particular cell by reference to the examples of the present application and through routine experimentation.

Preferably, the transient decrease in pressure that the cell is exposed to in the presence of the exogenous material is a decrease of at least 10 kPa, at least 100 kPa, at least 500 kPa or at least 1000 kPa. In certain embodiments, the transient decrease in pressure is a decrease in pressure (kPa) of at least 15, at least 20, at least 25, at least 30, at least 35, at least 40, at least 45, at least 50, at least 60, at least 70, at least 80, at least 90, at least 100, at least 150, at least 200, at least 250, at least 300, at least 350, at least 400, at least 450, at least 500, at least 550, at least 600, at least 650, at least 700, at least 750, at least 800, at least 850, at least 900, at least 950 or at least 1000.

The term "transient" in the context of a decrease in pressure means that the decrease in pressure occurs temporarily, in that after the cell is exposed to the decreased pressure, the pressure that the cell is exposed to afterwards will be of higher pressure. In some embodiments of the invention, the transient decrease in pressure means that the cells are exposed to a minimum pressure reached during a particular exposure for at least 10 nanoseconds, but no more than 1 millisecond. It would be understood that this time is not inclusive of the time between when the cell is exposed to a maximum pressure in a surrounding zone to the moment when the cell is exposed to a minimum pressure in a zone of lower pressure relative to the pressure of the surrounding zone. This time is also not inclusive of the time between when the cell is exposed to a minimum pressure in a zone of lower pressure to the moment when the cell is exposed to a maximum pressure in a surrounding zone.

The time that any one cell type can be exposed to the transient decrease in pressure will be determinable by the competent skilled addressee. Exposures that are too long may result in inefficiencies, while exposures that are too short may not allow for the introduction of the exogenous material into the cell. The optimum exposure times can be determined for a particular cell by reference to the examples of the present application and through routine experimentation.

Preferably, the cell is exposed to a transient decrease in pressure in the presence of the exogenous material for at least 10 nanoseconds, at least 100 nanoseconds, at least 1 microsecond or at least 1 millisecond. In certain embodiments of the invention, the cell is exposed to a transient decrease in pressure for at least 15 nanoseconds, at least 20 nanoseconds, at least 25 nanoseconds, at least 30 nanoseconds, at least 35 nanoseconds, at least 40 nanoseconds, at least 45 nanoseconds, at least 50 nanoseconds, at least 60 nanoseconds, at least 70 nanoseconds, at least 80 nanoseconds, at least 90 nanoseconds, at least 100 nanoseconds, at least 150 nanoseconds, at least 200 nanoseconds, at least 250 nanoseconds, at least 300 nanoseconds, at least 350 nanoseconds, at least 400 nanoseconds, at least 450 nanoseconds, at least 500 nanoseconds, at least 550 nanoseconds, at least 600 nanoseconds, at least 650 nanoseconds, at least 700 nanoseconds, at least 750 nanoseconds, at least 800 nanoseconds, at least 850 nanoseconds at least 900 nanoseconds, at least 950 nanoseconds, at least 100 microseconds, at least 200 microseconds, at least 300 microseconds, at least 400 microseconds, at least 500 microseconds, at least 600 microseconds, at least 700 microseconds, at least 800 microseconds, or at least 900 microseconds.

By "transient" is also meant that the decrease in pressure occurs relatively rapidly, in that the time between when the cell is exposed to a maximum pressure in a surrounding zone to the moment when the cell is exposed to a minimum pressure in a zone of relatively lower pressure is less than 1 second. In particular embodiments of the invention, the time between when the cell is exposed to a maximum pressure in a surrounding zone to the moment when the cell is exposed to a minimum pressure in a zone of relatively lower pressure is less than 1 millisecond. Similarly, once the cell is exposed to a minimum pressure in a zone of relatively lower pressure, the time between the cell being exposed to this minimum pressure and the time the cell is exposed to a maximum pressure in a surrounding zone is less than 10 seconds, 100 seconds or 1 minute. In the invention, the time between the cell being exposed to this minimum pressure and the time the cell is exposed to a maximum pressure in a surrounding zone is sufficient to permeabilise the membrane but not lyse the cell.

The cell may be exposed to more than one transient decrease in pressure in the presence of the exogenous material when a method of the invention is performed. In some embodiments, the cell may be exposed to more than one transient decrease in pressure wherein the transient decreases in pressure are the same or different in terms of the pressure differential between the zone of relatively lower pressure and a surrounding zone. In other embodiments of the invention, the pressure differential that defines the transient decreases may be due to the same or different minimum pressure in the zone of relatively lower pressure. The pressure differential that defines the transient decreases may also be due to the same or different maximum pressure in the surrounding zones.

For example, the cell may be exposed to a transient decrease in pressure wherein the pressure differential is 10 kPa, followed by a second transient decrease in pressure wherein the pressure differential is also 10 kPa. The first transient decrease in pressure of 10 kPa may be the result of the minimum pressure in the zone of relatively lower pressure being 50 kPa and the maximum pressure in the surrounding zone being 40 kPa, while the second transient decrease in pressure of 10 kPa may be the result of the minimum pressure in the zone of relatively lower pressure being 20 kPa and the maximum pressure in the surrounding zone being 30 kPa.

In another example, the cell may be exposed to a transient decrease in pressure wherein the pressure differential is 300 kPa, followed by a second transient decrease in pressure wherein the pressure differential is 80 kPa. The first transient decrease in pressure of 300 kPa may be the result of the minimum pressure in the zone of relatively lower pressure being 100 kPa and the maximum pressure in the surrounding zone being 400 kPa, while the second transient decrease in pressure of 300 kPa may be the result of the minimum pressure in the zone of relatively lower pressure being −50 kPa and the maximum pressure in the surrounding zone being 250 kPa.

In embodiments of the invention, the cell is exposed to the transient decrease in pressure in the presence of the exogenous material when both are in a liquid. The liquid may be any liquid that does not ordinarily result in lysis of the cell and, in some embodiments of the invention, is capable of maintaining the viability of the cell for the duration of the method. Preferably, the exogenous material would be soluble in, capable of being suspended in, or would be dispersible in, the liquid. For example, the liquid may be a cell growth media, or a buffered saline solution, such as phosphate buffered saline, or tris buffered saline. The liquid may be blood, plasma or serum or another bodily fluid, such as whole blood, cord marrow, bone marrow or adipose-derived fluids. The blood or bodily fluid may be fractionated, separated and/or diluted for improved processing. Although the fluid may contain agents or chemicals that promote the introduction of the exogenous material into the cell, the liquid need not necessarily contain any additional agents or chemicals to facilitate the introduction of the exogenous material into the cells. For example, in certain embodiments of the invention, the liquid does not comprise any additional cationic lipids, cationic polymers, calcium ions (for example, in the form of calcium chloride or calcium phosphate), magnesium ions (for example, in the form of magnesium chloride) or dendrimers. It would be understood that many of these chemicals and agents are toxic to cells, and the absence, or substantial absence of added amounts of these chemicals or agents in the liquid used in the method of the invention may prevent unwanted cell lysis or cell death when performing the method of the invention.

By "additional" is meant any additional amount of the chemical or agent in addition to what may normally and/or naturally be present in the liquid. For example, many bodily fluids, such as blood, may naturally comprise calcium ions, but in particular embodiments of the invention, no calcium phosphate would be added to the blood before being used as the liquid in a method of the invention. In another example, a cell growth media may normally comprise magnesium ions, but in particular embodiments of the invention, no magnesium chloride would be added to the growth media before being used as the liquid in the method of the invention.

In preferred embodiments of the invention, the cell is exposed to the transient decrease in pressure in a liquid within a channel, preferably an enclosed channel, with dimensions configured to allow the flow of the liquid comprising the exogenous material and the cell therethrough. In the context of the invention, by "channel" is meant any component with a length and two or more ends, with a hollow space extending the length of the component that allows the flow of a liquid through the hollow space, and through openings at the two or more ends. The dimensions of the channel need only be configured to allow the flow of a relevant cell type in said liquid. A cross-section of the channel may have any shape. The channel should comprise at least some enclosed sections but it is not necessarily sealed along the entirety of its length as long as there are areas within the channel in which the required pressure changes may occur.

It would be understood that the flow of the liquid would essentially be from one end of the channel to the other, and the direction of the flow would determine the orientation of what was "upstream" and "downstream".

Flow through the channel may be caused by various means, including but not limited to hydrostatic pressure, hydrodynamic pressure and/or electro-osmotic flow. The flow of the liquid may be driven by a pressure source, including but not limited to, a pressure pump, a gas cylinder, a compressor pump, a vacuum pump, a syringe, a syringe pump, a peristaltic pump, a piston, a capillary pump, a heart, a muscle or gravity.

The pressure source used to generate the flow of liquid through the channel would preferably provide steady-state flow such as creeping flow or laminar flow, as the liquid enters the channel. The skilled addressee would understand that creeping flow refers to a flow of liquid where the inertial forces of the liquid are significantly lower than the viscous forces of the liquid. Laminar flow refers to a flow of liquid where the inertial forces within the liquid are greater than or equal to the viscous forces of the liquid, but not great enough to induce transitional or turbulent flow in the liquid.

The flow of the liquid through the channel will have a velocity, and this velocity may be influenced by factors including, but not limited to, the configuration of the channel, the strength and nature of the pressure source, the viscosity of the liquid, the cell type and cell density in the liquid and/or the nature and amount of the exogenous material.

In preferred embodiments of the invention, the velocity of the liquid fluctuates as it flows through the channel, and the fluctuating velocity may be defined in terms of a maximum velocity and a minimum velocity of the liquid as it flows through the channel. The velocity of the liquid may fluctuate between a particular maximum and minimum velocity as the liquid flows through the channel. Preferably, the fluctuating velocity of the liquid flowing through the channel has a minimum peak velocity of 1 meter per second, or more preferably, 5 meters per second. In other preferred embodiments of the invention, the fluctuating velocity of the liquid flowing through the channel has a maximum velocity of 10 meters per second, a maximum velocity of 20 meters per second, a maximum velocity of 30 meters per second, a maximum velocity of 40 meters per second, a maximum velocity of 50 meters per second, a maximum velocity of 60 meters per second, a maximum velocity of 70 meters per second, a maximum velocity of 80 meters per second, a maximum velocity of 90 meters per second or a maximum velocity of 100 meters per second. Accordingly, it would be understood that the peak velocity of the liquid flowing through the channel may fluctuate between a range of 1 meter per second to 100 meters per second.

As the liquid flows through the channel, as well as the flow having a fluctuating velocity, the type of flow may change. For example, the flow may alternate between being laminar flow, creeping flow and unsteady flow where unsteady flow refers to a laminar vortex street, a transitional vortex street, a turbulent vortex street, transitional flow or turbulent flow. The skilled addressee would understand the difference between creeping flow, laminar flow and unsteady flow. In particular embodiments of the invention, the channel is configured to influence the flow of the liquid such that there are one or more regions within the channel where the flow of the liquid is laminar, one or more regions within the channel where the flow of the liquid is creeping, and one or more regions within the channel where the flow of the liquid is unsteady.

The type of flow may be estimated by calculating two different Reynolds numbers: one for a particular flow through an enclosed channel ($Re_c$) and/or region between a flow diverter, and one for flow around on object ($Re_o$). For example, for creeping flow, $Re_c$ is significantly less than unity ($Re_c \ll 1$) and for laminar flow, $Re_c$ is between unity and approximately two thousand ($1 < Re_c < 2000$). For example, for unsteady flow around an object, $Re_o$ is greater than approximately forty ($Re_o > 40$) or sufficient to induce unsteady flow. $Re_c$ may be defined as the ratio of the mean liquid velocity ($\bar{u}$) and the hydraulic diameter ($D_h$), to the kinematic viscosity (v) of the liquid, and this equation is defined below. For wide channels where the width is significantly greater than the height (or vice versa), $D_h$ may be substituted with twice the length of the shorter distance. When calculating the channel Reynolds number ($Re_c$) of flow between posts, this equation is used and the hydraulic diameter of the channel ($D_h$) refers to the hydraulic diameter of the channel between posts (FIG. 1) and the mean liquid velocity ($\bar{u}$) refers to the mean velocity between posts.

$$Re_c = \bar{u} D_h / v$$

In certain embodiments of the invention, the channel Reynolds number ($Re_c$) of the flow of the liquid in at least one of the regions within the channel where the flow of the liquid is laminar is at least 100, but no more than 2000. In certain embodiments, the channel Reynolds number ($Re_c$) of the flow of the liquid in at least one of the regions within the channel where the flow of the liquid is laminar is at least 100, at least 200, at least 300, at least 400, at least 500, at least 600, at least 700, at least 800, at least 900, at least 1000, at least 1100, at least 1200, at least 1300, at least 1400, at least 1500, at least 1600, at least 1700, at least 1800, at least 1900 or about 2000.

In preferred embodiments of the invention, the flow of liquid is influenced by one or more flow diverters within the channel. As used herein, a "flow diverter" is any element or member that results in the flow of the liquid through the channel being diverted in a localised region resulting in a localised region of decreased pressure, optionally coupled with unsteady flow.

In particular embodiments, the flow diverter is an obstacle placed in the channel. The term "obstacle" relates to any object placed within the channel that results in the flow of the liquid to be diverted around the object, resulting in a localised region of decreased pressure or decreased pressure coupled with unsteady flow substantially immediately downstream of the obstacle. The obstacle must be such that the cell can proceed through the channel beyond the obstacle. In preferred embodiments, the obstacle may extend outwards from an inner surface of the channel in a direction generally perpendicular to the length of the channel. The obstacle may extend from one side of the length of the channel to another side. Alternatively, the obstacle may only partially extend from one side of the length of the channel.

In certain embodiments of the invention, the obstacle has a width between 10 nanometers and 1 millimeter and all integer widths in between. In preferred embodiments, the obstacle has a width of more than 50 nanometers, more than 100 nanometers, more than 500 nanometers, more than 800 nanometers, more than 1 micrometer, more than 10 micrometers, more than 50 micrometers, more than 100 micrometers, more than 200 micrometers, more than 500 micrometers, more than 800 micrometers or about 1 millimeter. In preferred embodiments the obstacle has a width of less than 1 millimeter, less than 800 micrometers, less than 500 micrometers, less than 200 micrometers, less than 100 micrometers, less than 50 micrometers, less than 10 micrometers, less than 1 micrometer, less than 800 nanometers, less than 500 nanometers, less than 100 micrometers or less than 50 nanometers. In particularly preferred embodiments, the obstacle width is about 20 μm.

In particular embodiments, the obstacle is a post. In the context of the invention, an obstacle that is a "post" may be an obstacle that is a prism with a height greater than or equal to its greatest width. The post may be cylindrical, triangular, square, polygonal, wing-shaped or any other shape and the specific shape may be selected to tune the transient decrease in pressure for a given channel Reynolds number ($Re_c$) and/or unsteady flow for a given object Reynolds number ($Re_o$). In particularly preferred embodiments, the post is cylindrical.

The mean velocity of the flow through the channel and directly upstream of a flow diverter may be such that a transient decrease in pressure is induced just downstream of the flow diverter or a transient decrease in pressure and a localised region of unsteady flow is induced just downstream of the flow diverter. In embodiments of the invention wherein the flow diverter is a post, appropriate inducing mean upstream velocities may be calculated using the Reynolds number for the flow of the liquid around the post ($Re_o$). For the flow of a liquid around a cylindrical post, an $Re_o$ of at least forty ($Re_o \geq 40$) is likely to be required to induce unsteady flow downstream of the post. For other post geometries, the $Re_o$ required to generate unsteady flow will depend on the specific shape of post and the mean upstream liquid velocity would need to be tuned to create (1) a transient decrease in pressure of sufficient magnitude; or (2) unsteady flow and a transient decrease in pressure of sufficient magnitude. $Re_o$ is defined as the ratio of the mean upstream velocity ($\bar{u}$) and the characteristic length of the post (l) to the kinematic viscosity (v) of the fluid as shown below.

$$Re_o = \bar{u} l / v$$

In certain embodiments of the invention, the object Reynolds number ($Re_o$) of the flow of the liquid in at least one of the regions within the channel where the flow of the liquid is unsteady is at least 40, but no more than 2000. In certain embodiments, the object Reynolds number ($Re_o$) of the flow of the liquid in at least one of the regions within the channel where the flow of the liquid is unsteady is at least 40, at least 50, at least 60, at least 70, at least 80, at least 90, at least 100, at least 200, at least 300, at least 400, at least 500, at least 600, at least 700, at least 800, at least 900, at least 1000, at least 1100, at least 1200, at least 1300, at least 1400, at least 1500, at least 1600, at least 1700, at least 1800, at least 1900 or about 2000. In preferred embodiments the object Reynolds number ($Re_o$) of the flow of the liquid in at least one of the regions within the channel where the flow of the liquid is unsteady is less than 50, less than 60, less than 70, less than 80, less than 90, less than 100, less than 200, less than 300, less than 400, less than 500, less than 600, less than 700, less than 800, less than 900, less than 1000, less than 1100, less than 1200, less than 1300, less than 1400, less than 1500, less than 1600, less than 1700, less than 1800, less than 1900 or less than 2000.

Although not wishing to be bound by any particular theory, in embodiments of the invention wherein there is a localised region of unsteady flow substantially immediately downstream of a flow diverter, the cells may be exposed to a two-way increase in pressure as follows: (1) a localised increase in pressure caused by the unsteady flow; and (2) an increase in pressure following the transient decrease in pressure. This may create a pressure drop across the permeabilised cell membrane where the extracellular pressure is greater than the intracellular pressure and it may facilitate the active delivery of exogenous material near the cell membrane and/or exogenous material may be introduced into the cell by, for example, diffusion or flow from the local extracellular environment to the cytosol.

The positioning of any obstacle within the channel will generally result in regions of the channel with passages or gaps that the cells must pass through that are smaller in height, width or diameter than other regions of the channel. However, it would be understood that these regions with the smaller dimensions must still be configured such that the liquid comprising the exogenous material and the cell is still able to flow therethrough. In order to facilitate this, any gap created in the channel by an obstacle that is required to allow the liquid comprising the exogenous material and the cell to flow therethrough, would preferably be at least 1.01× the minimum diameter of said cell. It would be understood that cells are generally not perfectly spherical, and as such, the minimum diameter of a cell would be the minimum width of a cell when the shortest cross section is taken through the cell.

In particular embodiments of the invention, the gap has a width and height, or diameter, at least 1.01× the minimum diameter of the cell. In other embodiments, the gap has a width and height, or diameter, at least 2×, 5×, 10× or 100× the minimum diameter of the cell.

The invention also relates to devices for introducing exogenous material into a cell in a liquid comprising a channel with dimensions configured to allow the flow of said cell and exogenous material suspended in a liquid therethrough; and one or more flow diverter within said channel; wherein the flow diverter results in at least one region of decreased pressure immediately downstream of said flow diverter.

In particular embodiments of the invention, the device is a microfluidic device.

Suitably, the pharmaceutical compositions of the invention comprise an appropriate pharmaceutically acceptable carrier, diluent cryoprotectant, or excipient. Preferably the pharmaceutically acceptable carrier, diluent or excipient is suitable for administration to mammals and more preferably, to humans. By "pharmaceutically acceptable carrier" is meant a pharmaceutical vehicle comprised of a material that is not biologically or otherwise undesirable, i.e., the material may be administered to a subject along with the selected active agent without causing any or a substantial adverse reaction. Carriers may include excipients and other additives such as diluents, detergents, coloring agents, wetting or emulsifying agents, pH buffering agents, preservatives, and the like. Useful reference describing pharmaceutically acceptable carriers, diluents and excipients is Remington's Pharmaceutical Sciences (Mack Publishing Co. N.J. USA, 1991) and Remington: The Science and Practice of Pharmacy (Pharmaceutical Press, London, $22^{nd}$ Edition, 2012) which is incorporated herein by reference.

In embodiments that contemplate a cell suspension, it will be understood that the liquid of the suspension may be the liquid in a method of the invention was performed on, with or without additional components. A cell suspension may also refer to a dessicated or alternatively, a freeze-dried formulation as is understood in the art.

Unless defined otherwise, all technical and scientific terms used herein have the same meaning as commonly understood by those of ordinary skill in the art to which the invention belongs. Although any methods and materials similar or equivalent to those described herein can be used in the practice or testing of the invention, preferred methods and materials are described. For the purposes of the invention, the following terms are defined below.

The articles "a" and "an" are used herein to refer to one or to more than one (i.e., to at least one) of the grammatical object of the article. By way of example, "an element" means one element or more than one element. As used herein, the use of the singular includes the plural (and vice versa) unless specifically stated otherwise.

By "about" is meant a quantity, level, value, number, frequency, percentage, dimension, size, amount, weight or length that varies by as much 15, 14, 13, 12, 11, 10, 9, 8, 7, 6, 5, 4, 3, 2 or 1% to a reference quantity, level, value, number, frequency, percentage, dimension, size, amount, weight or length.

In the context of the invention, the words "comprise", "comprising" and the like are to be construed in their inclusive, as opposed to their exclusive, sense, that is in the sense of "including, but not limited to".

Some figures contain color representations or entities. Color illustrations are available from the Applicant upon request or from an appropriate Patent Office. A fee may be imposed if obtained from the Patent Office.

DETAILED DESCRIPTION OF PREFERRED EMBODIMENTS OF THE INVENTION

Although the invention has been described with reference to certain embodiments detailed herein, other embodiments can achieve the same or similar results. Variations and modifications of the invention will be obvious to those skilled in the art and the invention is intended to cover all such modifications and equivalents.

The invention is further described by the following non-limiting examples.

EXAMPLE 1

A method and device of the invention was assessed by transfecting a cell model with pcDNA 3.1 (Invitrogen™), which expresses green fluorescent protein (GFP). The device used was a microfluidic device configured with an array of posts, wherein the gap between posts was greater than the cell diameter.

Methods
Simulation & Analysis

Figure 1:
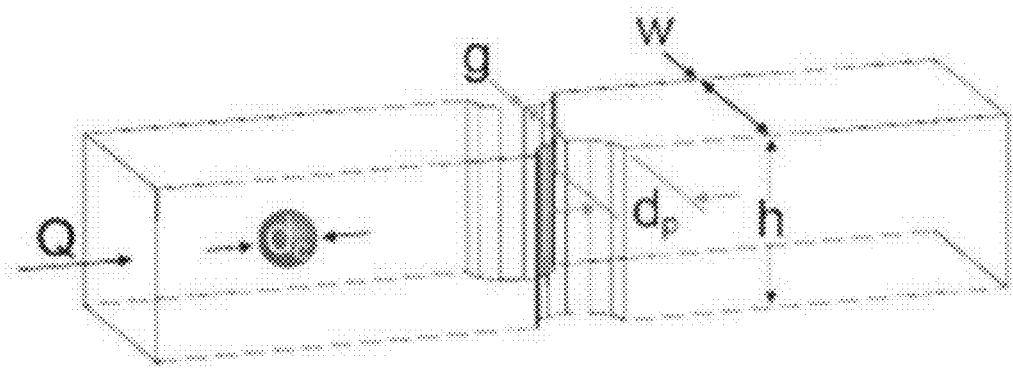
FIG. 1 shows an overview of unit geometry of a device according to an embodiment of the invention.

Simulation by computation fluid dynamics (CFD) with the finite-volume method was employed to examine the microenvironment around the gaps between posts for the parameters shown in Table 1 and the device geometry shown in FIG. 1. FIG. 1 shows an overview of unit geometry of a device according to the invention, where a liquid with a velocity (Q) enters the enclosed channel at an inlet, along with cells with a diameter ($d_c$) suspended in a liquid, wherein dc that is less than the gap width (g). Other variables represent post diameter ($d_p$), channel width (w) and channel height (h). Three-dimensional geometry was built in SolidWorks with an inlet length of 100 μm and an outlet length of 1000 μm for solving purposes. A structured mesh was constructed in ICEM CFD 14.5 and element quality was checked using the determinant, angle and aspect ratio. Solutions were obtained using ANSYS FLUENT 14.5 on a Windows 7 Enterprise 64-bit computer with an Intel Core i5-3470 CPU at 3.20 GHz and 16.0 GB of RAM. A coupled pressure-velocity solver was used to solve for velocity, pressure and shear stress contours. The channel Reynolds number (Rec) was calculated according to the parameters in Table 1, using the interior dimensions of the constriction and the equation below:

$$Rec = 2\rho Q/\mu(g+h)$$

The boundary conditions for the channel top, bottom and walls defined by posts were set to no slip. Boundary conditions for fluidic sidewalls were set to zero shear. Inlet velocity was defined by an average velocity and the outlet was set to a zero pressure boundary condition.

TABLE 1

Summary of experimental parameters.

| Parameter | Value |
| --- | --- |
| Cell type | HEK293 |
| Cell density | $1 \times 10^5$ cells ml$^{-1}$ |
| Cell diameter ($d_c$) | 13 μm |
| Floure scent molecule | pcDNA 3.1 (GFP plasmid) |
| Molecule density | 890 ng ml$^{-1}$ |
| Channel height (h) | 40 μm |
| Channel width (w) | 400 μm |
| Post diameter ($d_p$) | 20 μm |
| Post gap (g) | 30 μm |
| Row shift (s) | 0 μm |
| Row pitch ($p_r$) | 50 μm |
| Rows ($n_r$) | 9 posts |
| Column pitch ($p_c$) | N/A |
| Columns pitch ($n_c$) | 1 post |
| Media viscosity (μ) | $7.987 \times 10^{-4}$ Pa s |
| Media density (ρ) | 1,006 kg m$^{-3}$ |
| Flow rate (Q) | 5 ml min$^{-1}$ |
| Channel Reynolds number ($Re_c$) | 375 |
| Object Reynolds number ($Re_o$) | 131 |
| Oscillating frequency (f) | 44.4 kHz |

Transfection

Master moulds of microfluidic devices were fabricated using standard photolithography techniques, while devices were replicated using soft lithography and bonded to glass using oxygen plasma. An overview of the device design and transfection parameters are shown in FIG. 1 and Table 1 respectively.

HEK293 (Human embryonic kidney 293) cells were suspended in cell media at a density of $1 \times 10^5$ cells ml$^{-1}$, and pcDNA 3.1 GFP plasmids were seeded at a density of 890 ng ml$^{-1}$. This suspension was loaded into a syringe and pumped into the microfluidic device with a flow rate of 5 ml min$^{-1}$, which corresponds to a $Re_c$ of 375 at the gap between posts as the flow cell contained an array of 8 units separated with a 20 μm diameter post with a gap between posts of 30 μm. This also corresponds to a $Re_o$ of 131. Subsequently, cells were incubated for a period of 6 days then imaged via both fluorescent and optical microscopy to examine green fluorescent protein gene expression.

Results: Simulation & Analysis

Figure 2:
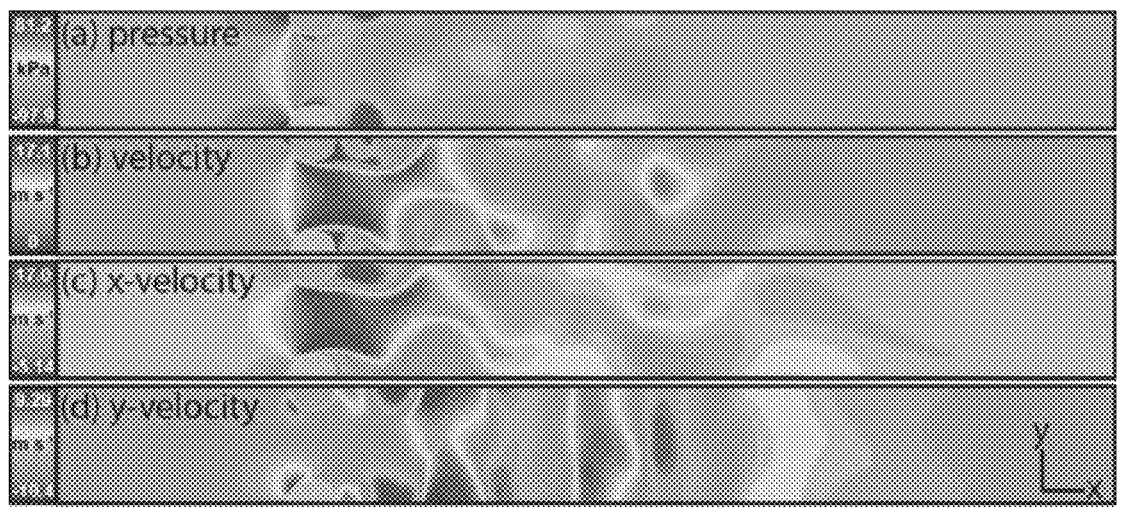
FIG. 2 shows an overview of the pressure changes that occur during simulations of an embodiment of a method of the invention.

Simulations indicated a high-pressure region occurs just upstream of the posts in the device of FIG. 1 and a decreased pressure region occurs just downstream of the posts. This means that as the cells flow past the posts, they are exposed a sudden and transient decrease in pressure. Additionally, these simulations were run as transient to determine if unsteady flow occurs. FIG. 2 shows an overview of the pressure changes that occur during simulations of an embodiment of the method of the invention showing (a) pressure contours, (b) velocity magnitude, (c) x-direction velocity of the liquid, which can be used to approximate cell velocity and (d) the y-direction liquid velocity with alternating jets due to unsteady flow. As shown in FIG. 2, there are significant flow velocities in the x-direction perpendicular to bulk flow in the y-direction in the enclosed channel, meaning unsteady flow is occurring.

According to the simulations, as a cell passed through a gap between posts positioned in the enclosed channel of the device, it moves from a surrounding zone with a localised pressure of 43.5 kPa, is exposed to a transient decrease in pressure of 94.3 kPa as it enters a zone of relatively lower pressure, which has a minimum pressure of 50.8 kPa. The magnitude of the transient decrease in pressure may vary depending on the phase of the oscillation. Additionally, cell velocity in the liquid is estimated to be 15 m s$^{-1}$ during this transient decrease in pressure, which occurs over a distance of approximately 40 μm for a transient decrease in pressure (dP/dt) of −35.4×10$^6$ kPa s$^{-1}$, wherein dP/dt is the change is pressure (dP) over change in time (dr). dP is change in pressure between local maxima and local minima, dt is change in time between local maxima pressure and local minima.

Subsequently, the unsteady flow conditions subject the cell rapidly changing flow velocities in the direction orthogonal (y-direction) to the direction the cell is moving (x-direction), as shown in FIG. 2d, where peak y-direction velocity ranges from −8.5 m s$^{-1}$ to 8.3 m s$^{-1}$ and these localised unsteady flows are approximately 20 μm wide. The magnitude of the localised unsteady flow decays as the cell moves away from the posts and decays completely after approximately 500 μm—in this space a cell is pulsed by approximately 5 unsteady flows with a velocity magnitude of between 3.4 m s$^{-1}$ and −8.5 m s$^{-1}$. During this period cell velocities are estimated to be between 10 m s$^{-1}$ and 15 m s−1 and unsteady flow widths are approximately 20 μm, indicating pulse times range between 2.0 μs and 1.3 μs. After the cell is pulsed with a transient decrease in pressure and the unsteady flow, the pressure increases to the same pressure as the outlet as the cell exits the microfluidic device or as the cell moves away from the gap.

The simulations suggest the exposure to unsteady flow creates a pressure drop across the cell membrane where the local extracellular pressure is greater than the local intracellular pressure, thereby facilitating active (mechanical) delivery. Additionally, the increase in pressure as the cell moves towards the device outlet suitably to facilitates active delivery due to the pressure drop across the permeabilised cell membrane.

Transfection

Figure 3:
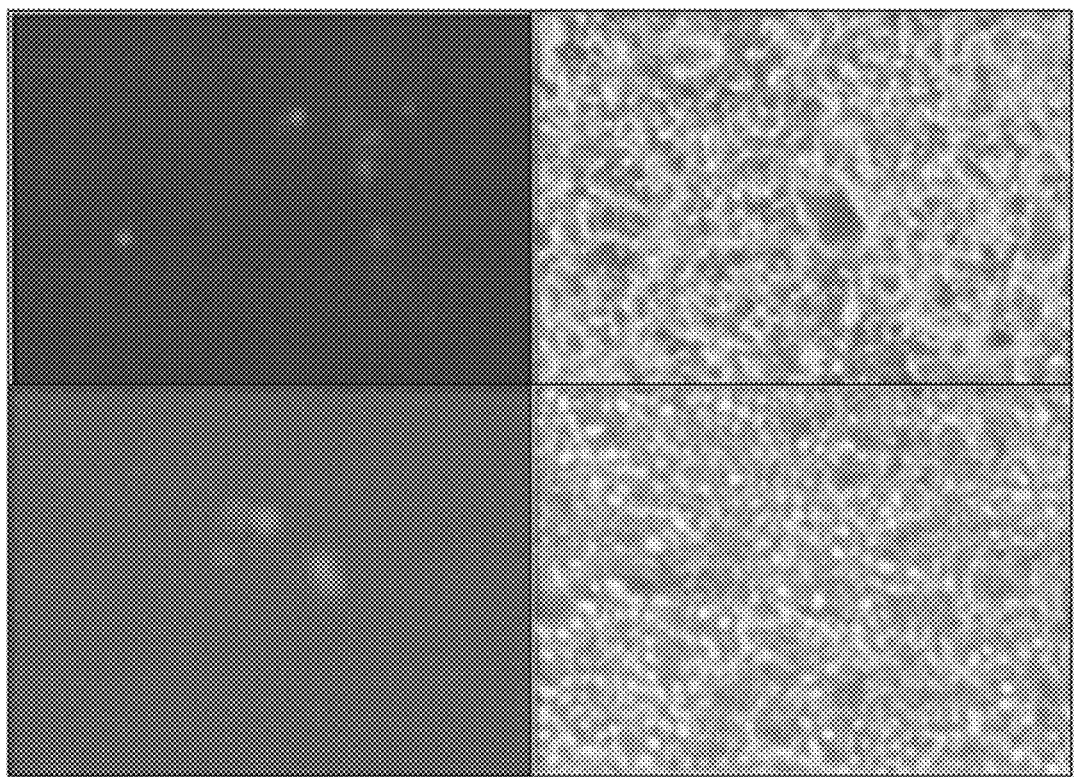
FIG. 3 is an overview of experimental transfection data taken by fluorescent microscopy (left) and optical microscopy (right) at a magnification of 20×, wherein HEK293 cells were transfected with pcDNA 3.1 in accordance with the parameters shown in Table 1.

As shown in FIG. 3, the use of a transient decrease in pressure and unsteady flow conditions through a post array can be used to transfect HEK293 cells with pcDNA 3.1 GFP plasmids. The images in the top row are taken from the same field of view as the images in the bottom row. Bright spots in images on the left-hand side of the panel represent HEK293 cells successfully transfected with pcDNA 3.1, which were viable and continued to express green fluorescent protein 6 days after transfection.

The simulations allow for unsteady flow, and preliminary simulations were used to determine which velocity was the most appropriate for calculating Re$_o$ based on the transition from laminar flow conditions to unsteady flow conditions. The velocity of the liquid used for calculating Re$_o$ varies in the literature, however, previous simulations confirm the mean upstream velocity is the appropriate velocity. For example, for liquid flow around a cylindrical post the object Reynolds number (Re$_o$) may be calculated with the equation below:

$$Re_o = \rho v \infty d / \mu$$

where v∞ refers to the velocity of a bulk liquid relative to the cylindrical post, and in this case, the mean upstream velocity of the liquid before the cylindrical post. This would be 8.68 m s$^{-1}$ for the parameters shown in Table 1, resulting in an Re$_o$ of 131.2.

In order to estimate the frequency of oscillation, the correlation shown below is used as it applies to flow of liquid around cylindrical posts, where the Re$_o$ is between 40 and 190. The Strouhal number (Sr) (a dimensionless number used to describe unsteady flow) maybe calculated from Re$_o$ with the following correlations for flow around a cylindrical post:

$$Sr = 0.2665 - 1.018/\sqrt{Re_o} \text{ for } (40 < Re_o < 190)$$

This calculation results in a Sr of 0.17, and the frequency of oscillation (f) may be calculated with the equation below with the liquid velocity (v) and characteristic length (L), which is equal to the diameter of the post (d$_p$):

$$f = Sr \, v/d_p$$

For the parameters described above, it is estimated the unsteady flow oscillates at a frequency of 44.4 kHz. These unsteady oscillations are also known to induce structural vibrations within the posts themselves. Thus, it is believed cells may be exposed to a transient decrease in pressure, 44.4 kHz unsteady flow along with induced structural vibrations.

Laminar flow (Re>>1) between one or more flow diverters, such as (but not limited to) posts, may be used to create a region of transiently decreased pressure substantially immediately downstream of the posts. This may be used to suddenly and temporarily decrease ambient pressure surrounding a cell as it flows past the posts of devices such as those shown in FIGS. 1, and 4 to 10. Additionally, if Re$_o$>40 then these flow characteristic are known to induce unsteady flow, and in the example describe above, this pulses cells with (1) a transient decrease in pressure and (2) unsteady flow. Moreover, this may be achieved using channel dimensions that are greater than cell dimensions (g>d$_c$) to mitigate clogging issues. This facilitates the transfer of exogenous material across the cell membrane and into the cytoplasm. According to Pawell et al (Pawell R. S., et al. (2013). Limits of parabolic flow theory in microfluidic particle separation: a computational study. ASME 4th International Conference on Micro/Nanoscale Heat and Mass Transfer, Hong Kong, China. December 11-14.) for channel Reynolds numbers above 100 (Re$_c$>100) between posts this creates a region of negligible shear stress. That is, under these conditions, membrane permeabilisation is not due to shear stress, which indicates that transfection may be a result of the transient decrease in pressure and unsteady flow conditions along with any conditions induced by the unsteady flow, such as structural vibrations in the posts, as observed by Renfer et al. (Renfer A., et al. (2013) Vortex shedding from confined micropost arrays. Microfluidics and Nanofluidics. 15(2): 231-242).

EXAMPLE 2

Experiments were performed to investigate the extent to which the magnitude and duration of the decrease in pressure affects transfection.

Methods

Two cultures of HEK293 cells were seeded at a density of 100,000 cells ml$^{-1}$, wherein culture 1 contained HEK293 cells and green fluorescent protein pcDNA 3.1 seeded at a density of approximately 900 ng $10^{-5}$ cells, and culture 2 contained HEK293 cells and 25-based pair oligonucleotides seeded at a density of 100 ng $10^{-5}$ cells. Both cultures were placed in a vacuum dessicator and the pressure decreased to −95 kPa over the course of 2 minutes. The vacuum was then released and returned to atmospheric pressure over the course of 10 seconds.

Results & Discussion

This experiment using a prolonged decrease in pressure resulted in nil transfection. No cells expressed GFP and the co-localisation of oligonucleotides and cells was negligible. When compared to Example 1, the magnitude of the decrease in pressure was substantially greater (a 95 kPa decrease, as opposed to a 20 kPa decrease in Example 1). However, the rate of decrease was substantially slower. In Example 1, it is estimated that the rate in which the transient decrease in pressure occurs (dP/dt) is −35.4×10$^6$ kPa s$^{-1}$. In the present example, the dP/dt is approximately −0.8 kPa s$^{-1}$. Accordingly, dP/dt may play a role in permeabilising the cell membrane as the cell membrane is gas permeable, such that if dP/dt is too low gas transfer will occur naturally through the cell membrane without permeabilising the membrane. Once dP/dt is sufficient, it is thought that the physical properties of cell membrane will not be able to accommodate for rapid gas transfer from the intracellular environment to the extracellular environment. Thus, the cell membrane may be stressed to a point where pores form, thereby allowing the introduction of exogenous material into the cell.

EXAMPLE 3

Figure 4:
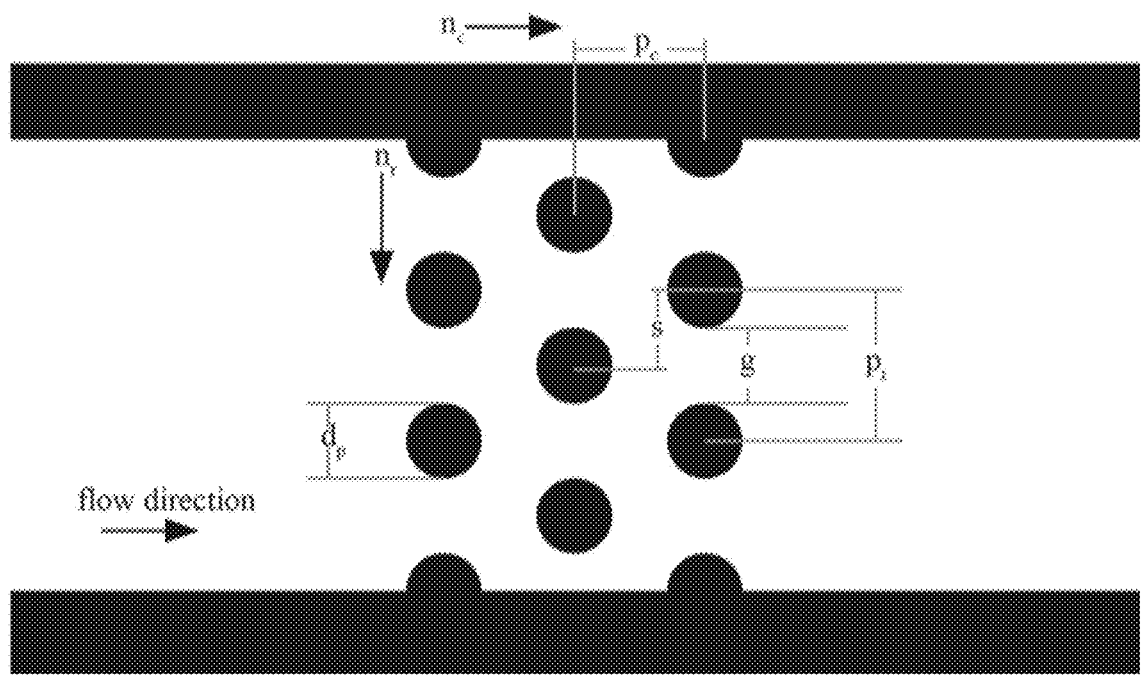
FIG. 4 is a schematic diagram of a microfluidic device containing three columns of posts ($n_c$=3) and four rows of posts ($n_r$=4) according to one embodiment of the invention.

FIG. 4 is a schematic diagram of a microfluidic device containing three columns of posts ($n_c$=3) and four rows of posts ($n_r$=4). The array is configured such that the diameter of the posts ($d_p$) is equal to the gap (g) between posts ($d_p$=g), and the posts for each column is shifted a sufficient distance to bifurcate flow from the previous gap where the shift distance (s) is equal to half row pitch (s=$p_r$/2) and the column pitch ($p_c$) is equal to the row pitch ($p_c$=$p_r$). The width of the channel, number of columns ($n_c$) and number of rows ($n_r$) will vary for each specific device using this or a similar design.

Figure 5:
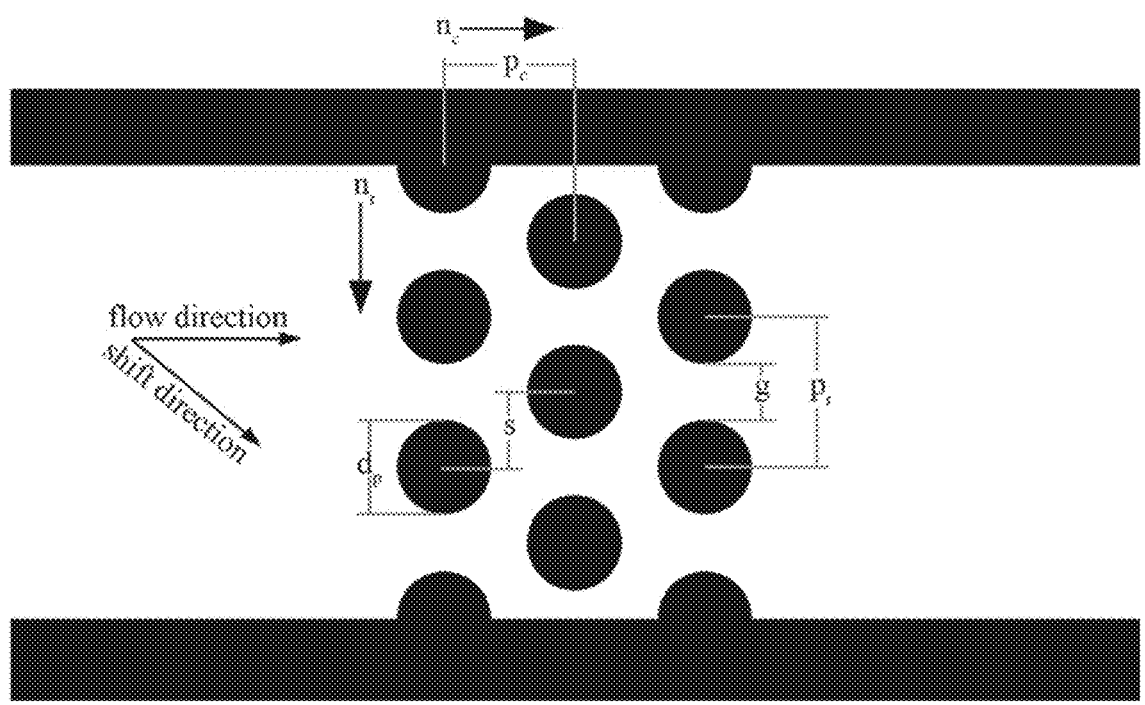
FIG. 5 is a schematic diagram of a microfluidic device containing three columns of posts ($n_c$=3) and four rows of posts ($n_r$=4) according to another embodiment of the invention.

FIG. 5 is a schematic diagram of a microfluidic device containing three columns of posts ($n_c$=3) and four rows of posts ($n_r$=4). The array is configured such that the diameter of the posts ($d_p$) is greater than the gap between posts (g), and the posts for each column is shifted a sufficient distance to bifurcate flow from the previous gap where the shift distance (s) is equal to half row pitch (s=$p_r$/2) and the column pitch ($p_c$) is equal to the row pitch ($p_c$=$p_r$). The width of the channel, number of columns ($n_c$) and number of rows ($n_r$) will vary for each specific device using this or a similar design.

Figure 6:
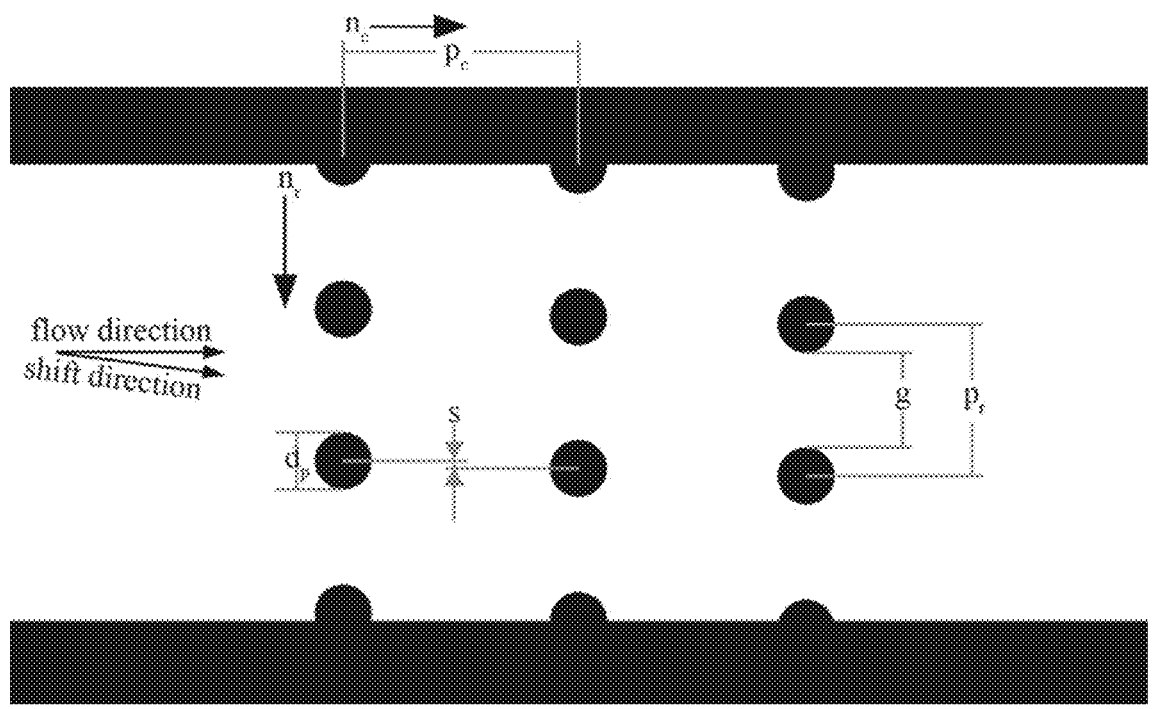
FIG. 6 is a schematic diagram of a microfluidic device containing three columns of posts ($n_c$=3) and four rows of posts ($n_r$=4) according to yet another embodiment of the invention.

FIG. 6 is a schematic diagram of a microfluidic device containing three columns of posts ($n_c$=3) and four rows of posts ($n_r$=4). The array is configured such that the diameter of the posts ($d_p$) is less than the gap (g) between posts (d<g), and the posts for each column is shifted slightly from the previous gap where the shift distance (s) is less than half the row pitch (s<$p_r$/2) and the column pitch ($p_c$) is greater to the row pitch ($p_c$>$p_r$). The width of the channel, number of columns ($n_c$) and number of rows ($n_r$) will vary for each specific device using this or a similar design.

Figure 7:
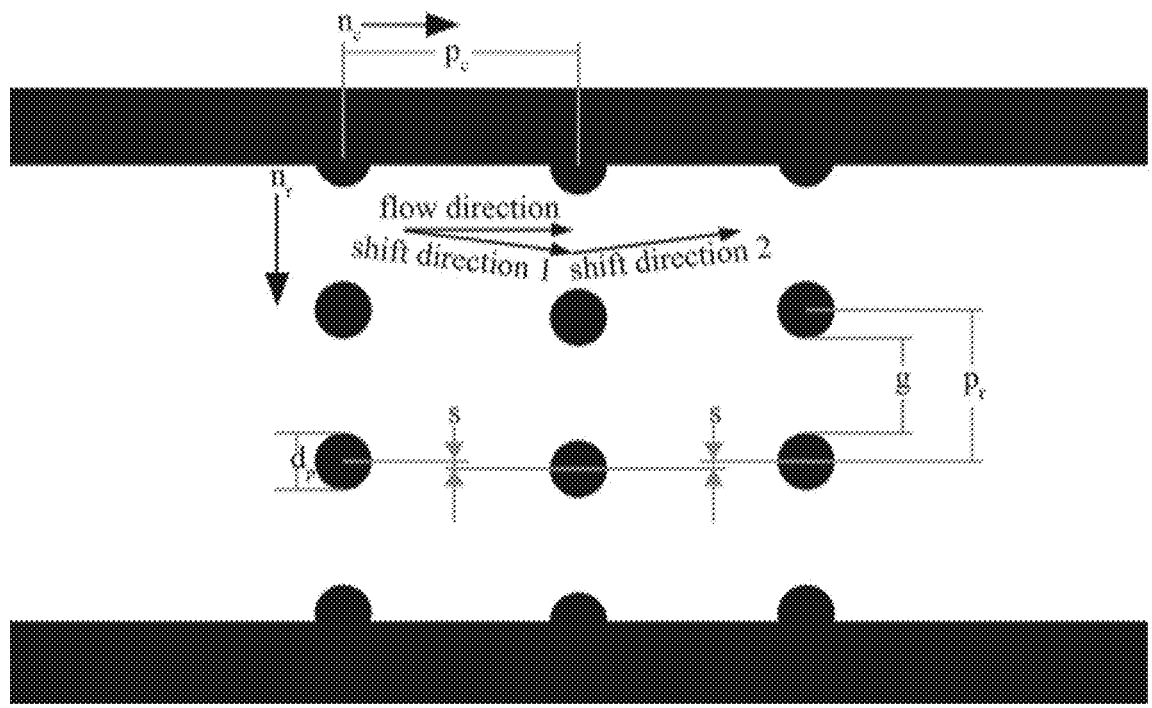
FIG. 7 is a schematic diagram of a microfluidic device containing three columns of posts ($n_c$=3) and four rows of posts ($n_r$=4) according to yet a further embodiment of the invention.

FIG. 7 is a schematic diagram of a microfluidic device containing three columns of posts ($n_c$=3) and four rows of posts (nr=4). The array is configured such that the diameter of the posts ($d_p$) is less than the gap (g) between posts of the posts ($d_p$<g), and the posts for each column is shifted slightly from the previous gap where the shift distance (s) is less than half the row pitch (s<$p_r$/2) and the shift direction switches with each row. The column pitch ($p_c$) is greater to the row pitch (pc>$p_r$). The width of the channel, number of columns ($n_c$) and number of rows ($n_r$) will vary for each specific device using this or a similar design.

Figure 8:
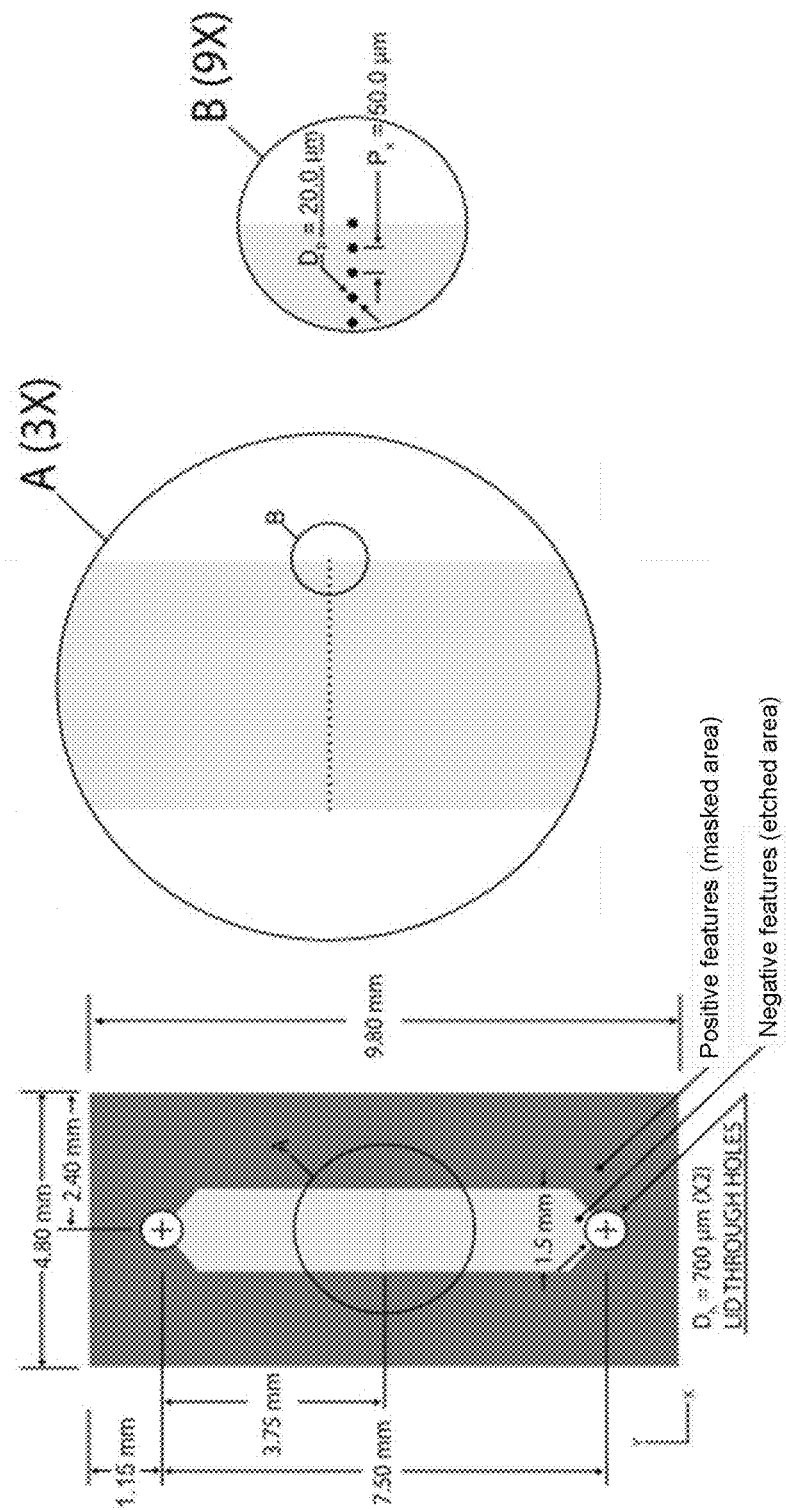
FIG. 8 is a sectional view of a device design according to a preferred embodiment of the invention. Panel A is an exploded view of the array design (3× magnification) whilst Panel B is an exploded view of the post design present on the array (9× magnification).
Figure 9:
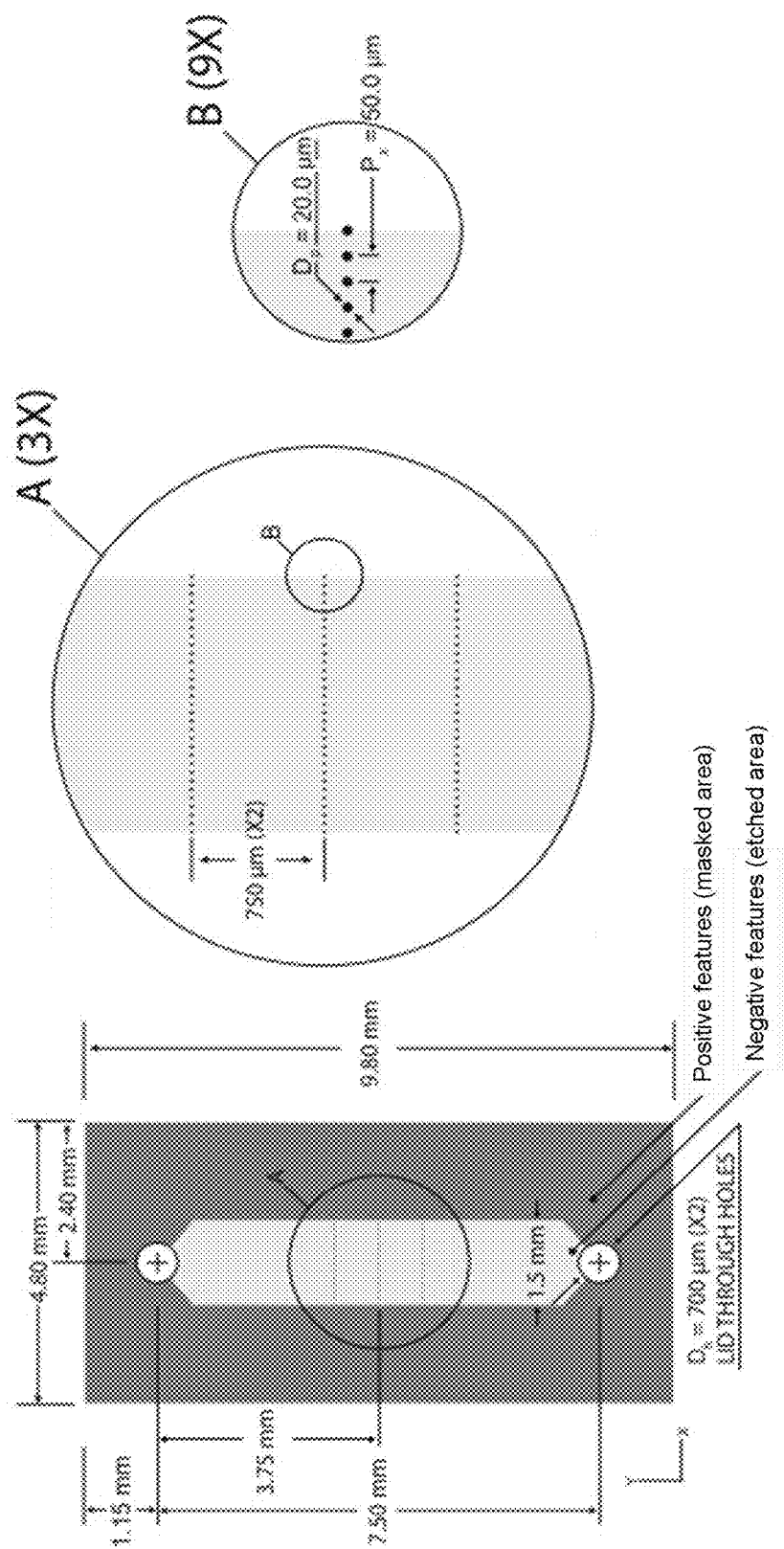
FIG. 9 is a sectional view of a device design according to another preferred embodiment of the invention. Panel A is an exploded view of the array design (3× magnification) whilst Panel B is an exploded view of the post design present on the array (9× magnification).
Figure 10:
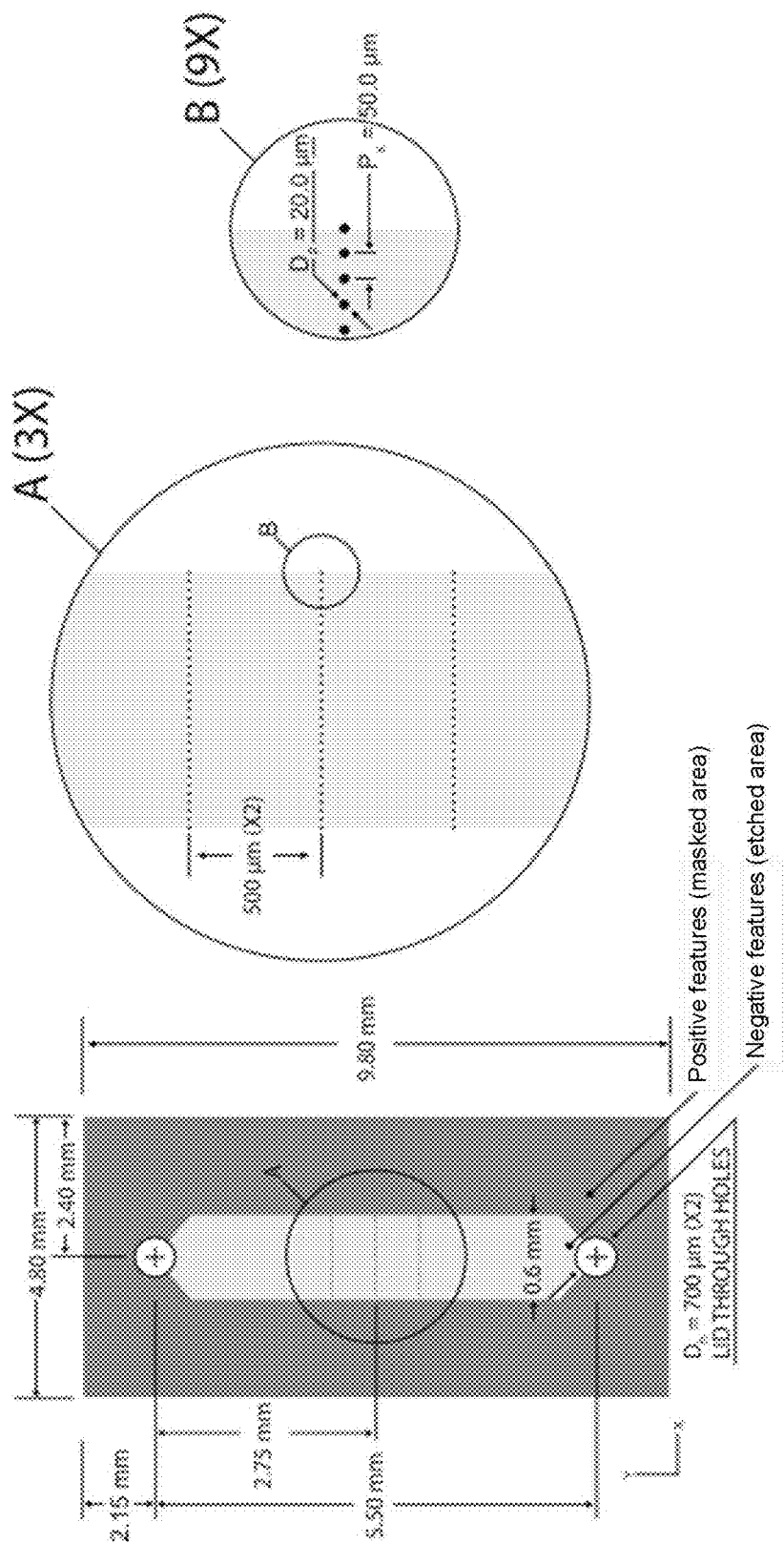
FIG. 10 is a sectional view according to yet another preferred embodiment of the invention. Panel A is an exploded view of the array design (3× magnification) whilst Panel B is an exploded view of the post design present on the array (9× magnification). The diagrammatic representations in FIG. 10 are not drawn to scale.

Preferred embodiments of a device design of the invention are depicted in FIGS. 8, 9 and 10. Both embodiments contain a single inlet and a single outlet with different internal post figurations that are particularly shown in Panels A and B of each figure. In these embodiments, all substrates are fused silica with a substrate thickness ($t_s$) of 700 μm. The unit includes a lid with 2 through-holes, each having a diameter ($D_h$) of 700 μm. The lid and substrate bond strength or burst pressure should be greater than (>>) 10 atm and once bonded, the total device has a thickness ($t_d$) of 1.40 mm. The device footprint of 4.80 mm×9.80 mm accounts for a dicing width of 200 μm. It is contemplated that 7×6 devices are arrayed across 70 mm×30 mm jig for a total of 42 devices. The bottom piece of the device is deep reactive ion-etched fused silica, bonded to a laser-machined fused silica wafer using a bulk material bond. For the embodiments shown in FIGS. 8 and 9, the substrate etched is to create a channel having a width of 1.5 mm, length of 7.5 mm and a depth of 40.0 μm. For the embodiment shown in FIG. 10, the substrate etched is to create a channel having a width of 0.6 mm, length of 5.5 mm and a depth of 40.0 μm.

According to the embodiment shown in FIG. 8, the array design (Panel A) includes thirty (30) posts in the x-direction ($n_x$) and one (1) row of posts in the y-direction ($n_y$) with an array pitch of 50.0 μm in the x-direction ($P_x$; otherwise referred to as the column pitch $p_c$). In this embodiment, the post design as shown in Panel B, is configured such that the diameter of the posts ($d_p$=20 μm) is less than the 30.0 μm gap of between the posts (gap=$P_x$−$d_p$) that is present in this embodiment.

According to the embodiment shown in FIG. 9, the array design (Panel A) includes thirty (30) posts in the x-direction ($n_x$) and three (3) rows of posts in the y-direction ($n_y$) with an array pitch of 50.0 μm in the x-direction ($P_x$; otherwise referred to as the column pitch $p_c$) and 750 μm in the y-direction (Py; otherwise referred to as the row pitch $p_r$). In this embodiment, the post design as shown in Panel B, is configured such that the diameter of the posts ($d_p$=20 μm) is less than the 30.0 μm gap of between the posts (gap=$P_x$−$d_p$) that is present in this embodiment.

According to the embodiment shown in FIG. 10, the array design (Panel A) includes twelve (12) posts in the x-direction ($n_x$) and three (3) rows of posts in the y-direction ($n_y$) with an array pitch of 50.0 μm in the x-direction ($P_x$; otherwise referred to as the column pitch $p_c$) and 500 μm in the y-direction (Py; otherwise referred to as the row pitch $p_r$). In this embodiment, the post design as shown in Panel B, is configured such that the diameter of the posts ($d_p$=20 μm) is less than the 30.0 μm gap of between the posts (gap=$P_x$−$d_p$) that is present in this embodiment.

Suitable ranges for particularly preferred embodiments of the invention as shown in the figures are provided below:

Post diameter range ($d_p$): 10 nm-5 mm;
Number of columns ($n_c$): 1-10,000;

Number of rows ($n_r$): 3-10,000;
Gap range (g): 10 nm-5 mm;
Shift (s): 0-5 mm;
Column pitch ($p_c$): 30 nm 50 mm; and
Row pitch ($p_r$) 30 nm-50 mm The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the invention. All such modifications and changes are intended to be included within the scope of the appended claims.

What is claimed is:

1. A method for introducing an exogenous material into a cell, comprising:
   introducing a liquid including the cell and the exogenous material into a flow channel of a microfluidic device, the channel including at least two flow diverters, the gap between the at least two flow diverters having a width, the width of the gap being greater than the diameter of the cell; and
   exposing said cell to a transient decrease in pressure and unsteady flow downstream of the flow diverters when the cell flows past the flow diverters to thereby introduce said exogenous material into said cell.

2. The method of claim 1, wherein the cell is viable after being exposed to the transient decrease in pressure and unsteady flow.

3. The method of claim 1, wherein said exogenous material is selected from the group consisting of a small organic molecule, a nucleic acid, a nucleotide, an oligonucleotide, a protein, a peptide, an amino acid, a lipid, a polysaccharide, a quantum dot, a carbon nanotube, a nanoparticle, a gold particle, a monosaccharide, a vitamin and a steroid.

4. The method of claim 1, wherein said exogenous material is introduced into the cytoplasm of said cell.

5. The method of claim 1, wherein said cell is a mammalian cell, a yeast cell or an insect cell and said exogenous material is introduced into the nucleus of said cell.

6. The method of claim 1, wherein said cell is exposed to said transient decrease in pressure in the presence of said exogenous material for at least 10 nanoseconds.

7. The method of claim 1, wherein unsteady flow is at least one of a laminar vortex street, a transitional vortex street, a turbulent vortex street, transitional flow or turbulent flow.

8. A method for introducing an exogenous material into a cell, comprising:
   introducing a liquid including the cell and the exogenous material into a flow channel of a microfluidic device, the channel including at least two flow diverters, the gap between the at least two flow diverters having a width, the width of the gap being greater than the diameter of the cell; and
   exposing said cell to a transient decrease in pressure and unsteady flow downstream of the flow diverters when the cell flows past the flow diverters to thereby introduce said exogenous material into said cell, wherein said transient decrease in pressure is at least 10 kPa.

9. The method of claim 1, wherein each flow diverter is a post.

10. The method of claim 9, wherein the post is cylindrical.

11. The method of claim 10, wherein the post has a diameter greater than the gap between the posts.

12. The method of claim 10, wherein the post has a diameter equal to the gap between the posts.

13. The method of claim 10, wherein the post has a diameter less than the gap between the posts.

14. The method of claim 1, wherein each flow diverter has a maximum width of 10 micrometers.

15. The method of claim 1, wherein each flow diverter has a maximum width of 100 micrometers.

16. The method of claim 1, wherein each flow diverter has a maximum width of 1 millimeter.

17. A method for transfecting a cell to introduce an exogenous material into the cell, comprising:
   introducing a liquid including the cell and the exogenous material into a flow channel of a microfluidic device, the flow channel having a width and at least two flow diverters oriented in an array along the width of the flow channel, each flow diverter having a maximum width, the maximum width of each flow diverter being greater than the gap between the at least two flow diverters; and
   exposing the cell to a transient decrease in pressure and unsteady flow downstream of the flow diverters when the cell flows past the flow diverters to thereby introduce the exogenous material into the cell.

18. The method of claim 17, wherein the at least two flow diverters include a plurality of posts.

19. The method of claim 17, wherein the maximum width of each flow diverter is 10 micrometers.

20. The method of claim 17, wherein each flow diverter has a height greater than its maximum width.

21. The method of claim 1, wherein the exogenous material introduced into the cell is an expression vector.

22. The method of claim 21, wherein the expression vector is a bacterial artificial chromosome (BAC).

23. The method of claim 1, wherein the cell is a mammalian cell having a nucleus and the exogenous material is introduced into the nucleus.

24. The method of claim 1, wherein the cell is exposed to the transient decrease in pressure and unsteady flow in the presence of the exogenous material for at least 10 nanoseconds.

25. The method of claim 1, wherein the flow has a maximum peak velocity of at least 1 meter per second.

26. The method of claim 1, wherein the flow of the liquid around the flow diverters has an object Reynolds number of at least 40.

27. The method of claim 17, wherein the cell is exposed to the transient decrease in pressure and unsteady flow in the presence of the exogenous material for at least 10 nanoseconds.

28. The method of claim 17, wherein the flow has a maximum peak velocity of at least 1 meter per second.

29. The method of claim 17, wherein the flow of the liquid around the flow diverters has an object Reynolds number of at least 40.

30. The method of claim 8, wherein the flow of the liquid around the flow diverters has an object Reynolds number of at least 40.

* * * * *